United States Patent [19]
Heineman et al.

[11] Patent Number: 5,240,571
[45] Date of Patent: Aug. 31, 1993

[54] QUANTITATIVE METHOD OF DETECTION OF ANALYTES IN AQUEOUS FLUIDS BY DETECTION OF NADH AND NADPH

[75] Inventors: William R. Heineman; Hua-Tang Tang, both of Cincinnati; H. Brian Halsall, Cleves; Amadeo J. Pesce, Cincinnati, all of Ohio

[73] Assignee: University of Cincinnati, Cincinnati, Ohio

[21] Appl. No.: 690,506

[22] Filed: Apr. 24, 1991

[51] Int. Cl.$^5$ ............................................. G01N 27/26
[52] U.S. Cl. ............................... 204/153.12; 204/403; 435/4; 435/14; 435/291; 435/817
[58] Field of Search ............... 204/403, 153.12; 435/4, 435/14, 15, 16, 18, 291, 817

[56] References Cited

U.S. PATENT DOCUMENTS

| | | |
|---|---|---|
| 4,042,462 | 8/1977 | Johnson et al. ........................ 435/15 |
| 4,045,297 | 8/1977 | Weeks et al. ........................... 435/15 |
| 4,956,276 | 9/1990 | Siddigi et al. .......................... 435/15 |
| 5,045,477 | 9/1991 | Belly et al. .............................. 435/4 |

OTHER PUBLICATIONS

Marilyn Dix Smith et al.: Analytical Chemistry, vol. 47, No. 7, Jun. 1975, pp. 1074–1077.

*Primary Examiner*—John Niebling
*Assistant Examiner*—Bruce F. Bell
*Attorney, Agent, or Firm*—Wood, Herron & Evans

[57] ABSTRACT

The concentration of NADH or NADPH in a test solution is determined by adding a redox coupling agent, preferably 2,6 dichloroindophenol DCIP, to the test solution. The coupling agent reacts with the NADH or NADPH to form an electroactive coupling agent (DCIPH$_2$) which is then detected electrochemically at a lower voltage than would be required to detect the NADH or NADPH. This can be used to detect NADH or NADPH formed by any well known enzymatic or immunoassay method which produces NADH as a detectable product. This has particular application to biological fluids such as whole blood which does not require any treatment of the test sample prior to electrochemical analysis. In particular, red blood cells do not have to be removed from whole blood samples to provide reliable data.

11 Claims, 5 Drawing Sheets

QUANTITATIVE METHOD OF DETECTION OF ANALYTES IN AQUEOUS FLUIDS BY DETECTION OF NADH AND NADPH

BACKGROUND OF THE INVENTION

There are literally hundreds of millions of tests of aqueous fluids conducted each year. This is particularly true in the medical field where urine, blood, serum, and other bodily fluids are tested for literally hundreds of different substances.

Many of these substances can be detected using particular electrodes with membrane bound enzymes which react with a substance to be detected and produce a detectable product such as hydrogen peroxide or oxygen. Such electrode systems are reliable but very limited in application. Since a membrane bound enzyme is required, the electrode is dedicated for analysis for one particular substance. This in turn causes the testing to be relatively expensive.

There are a number of different enzymatic assays and immunoassay that are employed which produce a nicotinamide adenine dinucleotide such as nicotinamide adenine dinucleotide (NADH) or nicotinamide adenine dinucleotide phosphate (NADPH) as products in quantitative amounts which can then be detected. These detection systems currently rely on photometric detection of NADH and NADPH.

Photometric detection of NADH and NADPH is problematic. Depending on the fluid being tested, various pretreatment steps are required in order to permit the NADH or NADPH to be detected photometrically. For example, if the sample is blood, red blood cells will interefere with colorimetric detection systems. Therefore, the blood cells must be removed. If a sample incorporates excessive amounts of protein, lipid, bilirubin or hemoglobin, these can interfere with certain photometric detection systems. Thus, depending on the particular test required, the sample will require various pretreatments. This requires unique treatment of each sample for each test method. This significantly increases the difficulty and the expense of sampling.

Particularly in hospitals this presents additional problems. Handling of any bodily fluid is potentially hazardous. Worker safety is extremely important and any time a bodily fluid such as blood is handled, there is a potential that the worker will be infected with a virus, such as the AIDS virus or hepatitis. Therefore, it is desirable to minimize any handling of these hazardous test samples.

NADH and NADPH are theoretically detectable using electrochemical analysis. Direct oxidation of NADH or NADPH is an attractive method, but it has general limitations. First, the high applied potential necessary for the direct oxidation of NADH and NADPH due to the large over-voltage at solid electrodes compromises selectivity due to interfering oxidation reactions from serum components, such as uric acid, ascorbic acid, and acetaminophen. Second, the detection limit of an electroanalytical technique is generally not as good at such a positive potential due to high background currents. Further, proteins associated with certain samples can coat an electrode surface and thereby inhibit the detection of NADH or NADPH.

The large positive potential required to oxidize NADH at a solid electrode is due to the overpotential associated with a slow heterogeneous electron transfer. This overpotential has been diminished by chemical modification of the electrode with appropriate catalysts such as orthoquinones covalently bound to the carbon electrode, phenazonium salt adsorbed on graphite, dopamine covalently attached to vitreous carbon, catechols with pyrene side chain adsorbed on graphite and amide linked 3,4 dihydroxy benzylamine and vinyl polymerized eugenol immobilized physically on carbon. Nile blue has been coupled with terephthaloyl chloride to form a compound that adsorbs to graphite electrodes and shifts the NADH oxidation wave to $-0.15$ volts. However, the catalytic action of these electrodes has generally proven to be too short lived for their practical use in a flow system or repetitive analysis of many samples containing NADH. Accordingly, electrochemical analysis of NADH and NADPH has proved unsatisfactory and therefore photometric methods have been required with all their attendant disadvantages.

SUMMARY OF THE INVENTION

The present invention is premised on the realization that NADH and NADPH can be detected electrochemically in an aqueous sample by combining the sample with a redox coupling agent.

More particularly, the present invention is premised on the realization that where a redox coupling agent having a redox potential of from about 400 millivolts to about $-200$ millivolts versus a reference electrode of Ag/AgCl (3M KCl) at testing pH, and preferably from about 0 to about 300 millivolts, effectively permits the quantitative electrochemical detection of NADH or NADPH in a test solution. These redox coupling agents include quinones, quinoneamines, phenylene diamine, indophenols, phenazines and phenoxazines In a preferred embodiment, the redox coupling agent is 2,6-dichloroindophenol and when combined in aqueous solution with a test sample permits electrochemical quantitative analysis of NADH or NADPH. This permits quantitative detection of NADH or NADPH in samples such as amniotic fluid, urine, serum, whole blood (including icteric, hemolytic and lipemic samples), and the like without prior purification steps. Thus, this invention can be used in combination with currently used enzymatic assays and immunoassays to detect dozens of analytes.

Further, by adding an effective surfactant, samples containing large quantities of proteins (and other surface active components) can be analyzed for the concentration of NADH or NADPH in a mobile phase flowing over a stationary electrode without fouling of the electrode.

The detection method is particularly reliable and sufficiently sensitive permitting the fluid sample to be diluted which also prevents fouling of the electrode surfaces.

The objects and advantages of the present invention will be further appreciated in light of the following detailed descriptions and drawings wherein:

DETAILED DESCRIPTION

According to the present invention, NADH or NADPH (which are both nicotine amide adenine dinucleotides) are quantitatively detected using an electrochemical analyzer by combining NADH or NADPH with an appropriate redox coupling agent in aqueous solution and passing this through the electrochemical analyzer, i.e., an amperometric detector. The NADH or NADPH may be produced in an enzymatic assay or immunoassay of an analyte in the test solution. The test solution would be combined with other reagents from an assay kit to form NADH or NADPH and combined with the redox coupling agent. The dinucleotide would then be detected according to the present invention.

The solutions tested according to the present invention must be aqueous fluids. They can include a wide range of aqueous fluids including water, protein containing fluids such as milk and the like and tannin containing solutions such as wine and juices. However, the present invention is primarily applicable to testing biological fluids such as urine, serum, amniotic fluid, blood and the like.

The analytes which can be quantitatively detected according to the present invention include any substances which can be reacted with any of a variety of different reagents to produce quantitative amounts of the dicucleotides NADH or NADPH.

Enzyme assay methods which are designed to produce the dinucleotides are commercially available. Such tests detect uric acid, lactic acid, pyruvic acid, ascorbic acid, theophylline, phenytoin as well as carbon dioxide, glucose -6- phosphate, alpha ketoglutarate, glycogen, inorganic phosphate, acetoacetic acid, galactose -1- phosphate, uridyltransferase, beta hydroxybutyrate, aspartate aminotransferase, creatine kinase, alanine amino-transferase, isocitric dehydrogenase, glycero -P-dehydrogenase, ADP and AMP alanine, asparate, ATP and P-creatine, citrate, dihydroxyacetone phosphate.

Several of commercial kits, for example, include the enzyme multiplied immunoassay technique EMIT sold by Syva Company, Palo Alto, Calif., as well as the Clinical Chemistry test kits sold by Abbott for diagnostics for use with the Abbott TDX analyzer (without the use of the fluorometric components) as well as those sold by Boerhinger Mannheim Corporation, Baxter Laboratories, Beckman Instruments and DuPont Technician.

The EMIT brand assay produces NADH as an indicator of the following: carbamazepine, ethosuximide, phenobarbital, phenytoin, primidone, valproic acid, theophylline, caffeine, digoxin, disopyramide, lidocaine, n-acetylprocainamide, procainamide, quinidine, amikacin, chloramphenicol, gentamicin, netilmicin, tobramycin, vancomycin, amitriptyline, imipramine, desipramine, thyroxine, acetaminophen, amphetamine/methamphetamine, barbiturate, benzodiazepine, cannabinoid, cocaine, methaqualone, methadone, opiate, phencyclidine, and propoxyphene.

The various Abbott TDX brand assays are used to generate NADH or NADPH as an indicator for the following: glucose, cholesterol, HDL cholesterol, iron/TIBC (total iron binding capacity), uric acid, lactate dehydrogenase, blood urea nitrogen (BUN) actually serum urea nitrogen, triglycerides, creatinine, lactic acid, and ethanol.

These assays are very well known and are discussed in various references such as *Methods in Clinical Chemistry*, C.V. Mosely Company (1987) and *A Flexible System for Enzymatic Analysis*, Academic Press (1972).

For use in the present invention, the redox coupling agent must be one which has a redox potential of from about 400 millivolts to about −200 millivolts and preferably is one which has a redox potential of about 0 to 300 millivolts and more preferably 0 to 100 millivolts. These potentials are versus a Ag/AgCl electrode (3M KCl) at testing pH.

Redox coupling agents, according to the present invention, include such compositions that have the redox potential within this range. These are generally hydroxy or amine substituted aromatic compositions. Such agents include quinones, quinone amines, phenylene diimines and their derivatives and large molecular reagents that incorporate necessary functional elements of these compounds including indophenols, phenazines and phenoxazines. Of these many compounds, 2,6 dichloroindophenol (DCIP) or a salt thereof such as the sodium salt is preferred.

DCIP is thought to react with NADH according to the following formula:

DCIP + 2 NADH → 2AND+ + DCIPH$_2$

DCIPH$_2$ is the elctroactive coupling agent which can be detected with an amperometer.

The aqueous test sample fluid such as whole blood or serum is combined with the enzymatic immunoassay reagent to cause the reduction of AND+ to NADH or NADP+ to NADPH. The NADH or NADPH is proportional to the amount of analyte present in the specimen. The coupling agent is introduced and is converted into the electroactive product. The oxidation of the electroactive product is measured amperometrically at 0 to 300 mV and preferably 150 to 50 mV vs. Ag/AgCl by amperometric equipment. A standard curve is prepared by using a number of known concentrations of the analyte to be tested and the concentration of the analyte in the unknown sample is determined by reference to this standard curve.

In a preferred, but not exclusively applicable electrochemical detection method, the rate of the production of the electroactive coupling agent is measured by injection thereof into a flowing stream which passes over an electrode, this being maintained at a potential such that some or all of the electroactive coupling agent is oxidized when the flow is under the influence of the electrode. The current resulting from this redox reaction in the amperometric detector is proportional to the concentration of electroactive agent, which is in turn related to the concentration of analyte present in the sample. Accordingly, a sample can be analyzed by simply measuring a current signal, and this method of detection is extremely sensitive and capable of determining very low levels of product.

Figure 1:
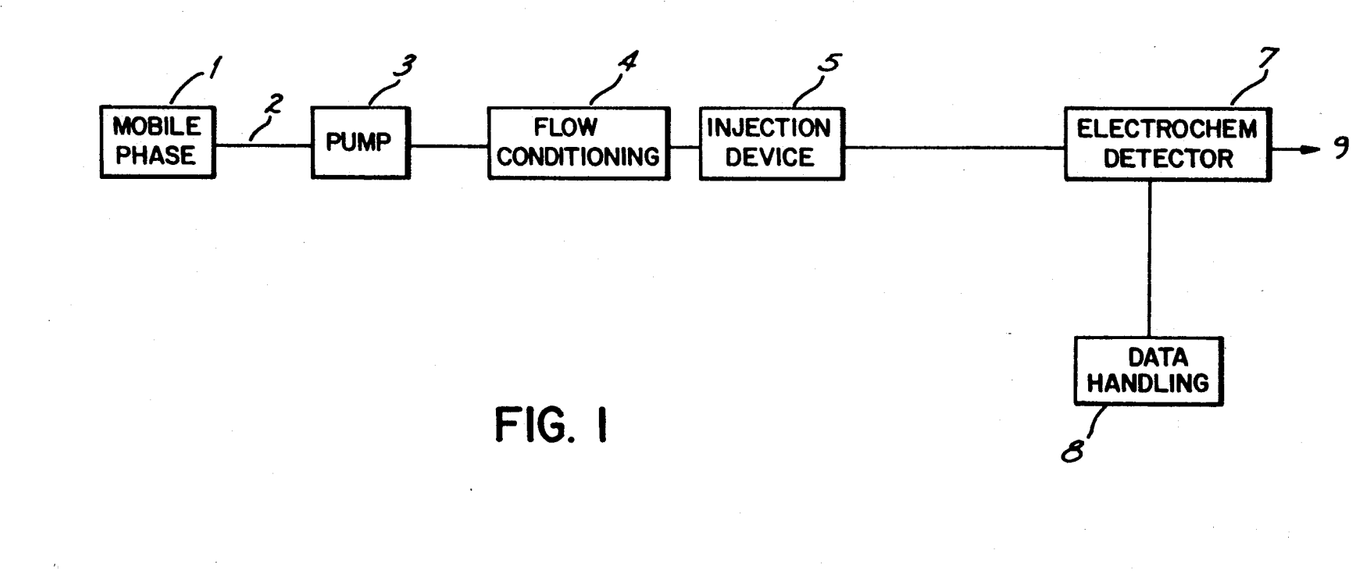
FIG. 1 is a diagrammatic depiction of the operation of the present invention.

A block diagram of an exemplary electrochemical apparatus is found in FIG. 1. A mobile phase 1 comprising water, organic solvents and/or various organic and/or inorganic salts can be degassed, if desired, and filtered by conventional procedures prior to use. This fluid serves to transport the samples and various constitutents thereof through the apparatus in conjunction with a pump 3, generally operated at constant flow rates of 0.01 to 10.0 milliliters per minute during the entire operating time of the apparatus.

This pump may be any one of several different designs, including peristaltic, single- or multiple-reciprocating pistons, or syringe types. An optional flow conditioning module 4 may be added in high sensitivity applications.

A sample which contains at least the analyte and the coupled mixture of AND+/NADH or NADP+/NADPH and coupling agent/electroactive coupling agent is injected into the constant flow stream by the use of a sample injection device. This device may consist of a manually operated injection valve or syringe loaded septum injection port, or an automatic sampler in which the samples are transferred mechanically, in an automatic, controlled fashion without further human intervention. The sampling device is designed to inject a reproducible volume of the sample, typically 1-200 microliter in size.

The sample is transported by the steady state flow of the mobile phase to the electrochemical detector. This device detects the analyte to be measured by its oxidation or reduction current at the electrical potential(s) selected by the user. While the processing of the signal peaks may be accomplished by using a common strip chart recorder and manually measuring the peak height, which is proportional to concentration, it is often convenient to further simplify the operator's task by using a microprocessor-based unit 8 which can integrate peak area, calculate concentration from a calibration table and print out the original concentration of the analyte to be measured.

After detection, mobile phase is discarded upon exit to a waste receptacle 9.

The test sample may be preliminarily treated using an assay kit which will produce NADH or NADPH. For example, if lactate is measured the kit may include lactate dehydrogenase which will react with lactate and AND+ to form pyruvate and NADH. The amount of NADH formed and the rate of formation are proportional to the lactate acid concentration. Alternately, lactic dehydrogenase itself can be measured by adding lactate acid plus AND+ which will convert to pyruvate and NADH which can be measured.

The enzyme glucose -6- phosphate dehydrogenase can be used again to proportionably produce NADH. There are literally hundreds of such assay kits which produce proportionate amounts of NADH or NADPH relative to a particular analyte.

The test sample with the produced NADH or NADPH is then combined with the redox coupling agent. Generally an excess amount of redox coupling agent is added. Accordingly, if the test sample is expected to have $10^{-8}$ to $10^{-3}$ molar concentration of NADH, the concentration of coupling agent must be at least equal to the upper limit. Therefore, $10^{-3}$ molar coupling agent must be added. Generally excess coupling agent is added. The sample then can be injected into the electrochemical analyzer.

In applications where the concentration of NADH formed exceeds $10^{-8}$ molar (the lower detection unit of NADH), the sample can be diluted with saline or a buffer solution such as phosphate. This may be preferred for biological test samples to reduce fouling of the electrode.

The pH of the test solution will vary depending on the assay employed to produce the NADH. The reaction of DCIP and NADH is accelerated at lower pH's, i.e., about 2. However, background interference is lowest at pH of 7. Therefore, one can choose the pH used during the electrochemical analysis, i.e., the test pH. Generally a pH of 7 is preferred; although the pH can be from 2 to about 9.

When testing biological fluids such as blood, it is preferred to add a surfactant to the fluid to prevent associated proteins from being deposited onto the electrode surface. Generally, a low concentration of surfactant is added, generally from about 0.01 to about 0.5% by volume.

In this application, anionic, cationic and nonionic water soluble surfactants can be employed. There are many different types of nonionic surfactants. Generally any which will effectively disperse proteins can be used in the present invention. Typical nonionics include the ethoxylated aliphatic alcohols such as the Neodol brand and Tergitol brand, the alkyl ethoxylates such as the Igepal brand and the ethylene oxide propylene oxide copolymers such as Pluronic. Suitable anionic surfactants include the linear alkyl sulphonates and the alkyl ethoxylate sulphates as well as the tallow alkyl sulphates.

The preferred surfactant is a nonionic surfactant specifically the polyoxyethylene derivatives of fatty acid partial esters of hexitol anhydrides. These are sold under the trademark Tween and generally the surfactant Tween 20 is preferred.

In the following examples, the use of the preferred redox coupling agent 2,6 dichloroindophenol (DCIP) is employed. These demonstrate both the effectiveness of the present invention as well as many of the advantages of the present invention.

EXAMPLE 1

A Fisher (Pittsburgh, Pa.) Model 1500 pipetter/diluter was used in procedures involving the theophylline kits and the handling of patients' samples. The flow injection system (FIA-EC) was a Bioanalytical System CS-2 (BAS, W. Lafayette, Ind.) employing an LC-4B Amperometric Detector (BAS) and a Fisher Recordall 5000 recorder. A 20 microliter sample loop was used. The electrochemical cell in this system was a thin-layer cell with a glassy carbon working electrode (BAS RC-2A), a Ag/AgCl reference electrode (BAS RE-1) and a stainless steel auxiliary electrode. All potentials are reported vs Ag/AgCl (3 mol/L KCl) reference electrode. Reactions took place in disposable 2.0 mL polystyrene cups with a conical bottom (Fisher Scientific). A stop watch was used to time the kinetic measurements. Measurements were made at 23° C. (room temperature).

Assay components were diluted according to the manufacturer's instructions, except that before taking measurements, a 50 microliter aliquot of the enzymatic reaction mixture and 100 microliters of pH 8.0 buffer were added to 350 microliters of DCIP solution at 1 and 9 minutes, respectively, and allowed to react with DCIP for 7 minutes. The resultant solutions were injected into the FIA-EC system, and the current responses were measured at +200 mV. The time intervals were chosen for the total sample throughput and the convenience of manual operation. Both calibrators and test samples were assayed in duplicate. The mean value of the current peak heights of each sample was taken as the corresponding signal difference.

The recovery of theophylline from normal serum by the procedure was assessed by adding theophylline to pooled serum prepared from patients not undergoing theophylline treatment and which showed zero theophylline concentration when measured by the fluorescence polarization immunoassay (FPIA) method. 50 microliters of the theophylline aqueous solution were added to 1.00 mL of pooled serum to yield the required drug concentration in serum. Recoveries of theophylline from hemolytic (hemoglobins =199 mg/dL), icteric (bilirubin =14.4 mg/dl), and lipemic (triglycerides =1190 mg/dL) sera were also performed with the same procedure. Intra- and inter-assay precisions were obtained by measuring three sera with low, medium, and high drug concentrations.

Figure 2:
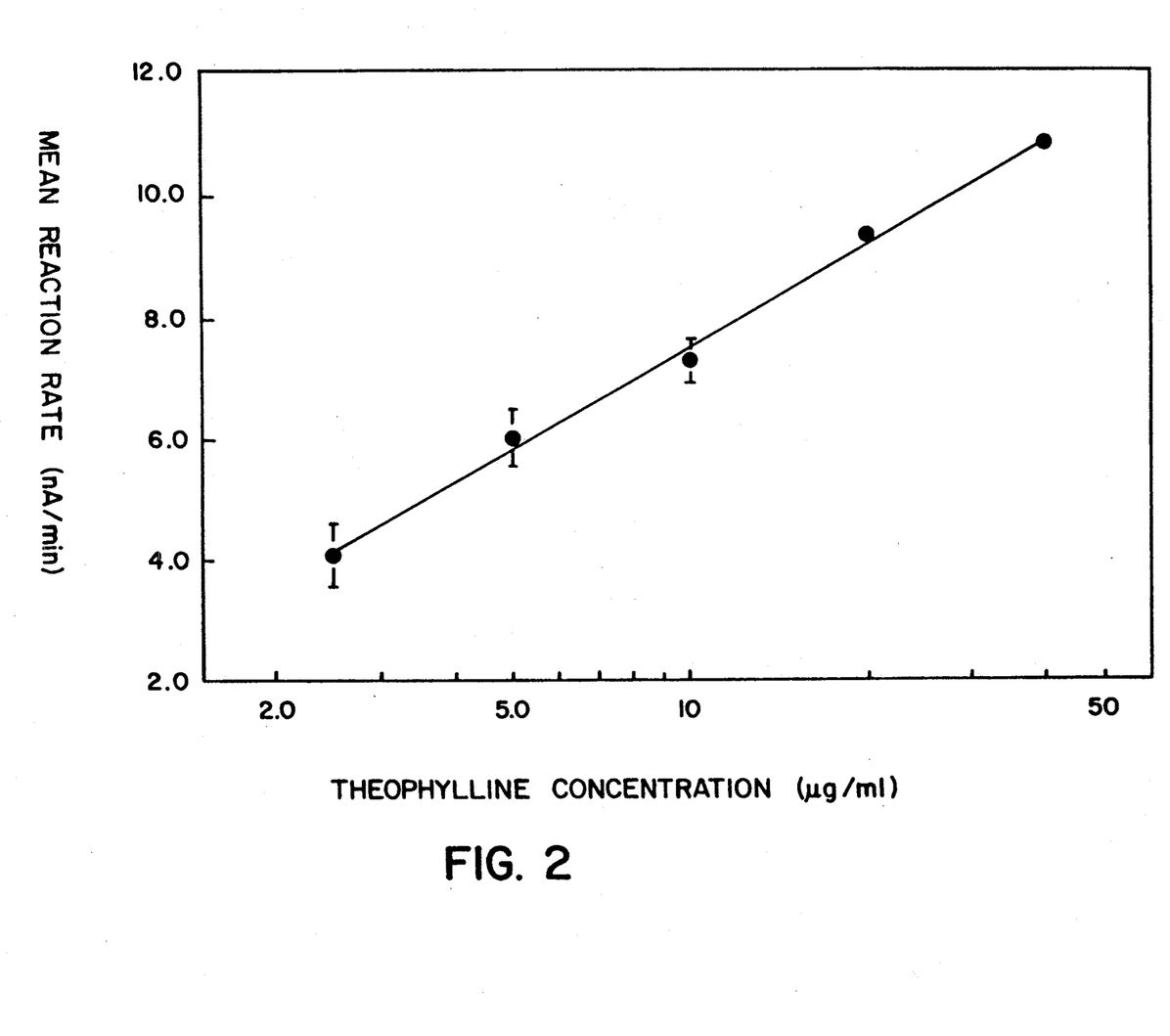
FIG. 2 is a graph showing the test results obtained from example 1.

FIG. 2 shows a typical standard curve for the measurement of theophylline by electrochemical EIA in serum. The peak current response was linearly proportional to the logarithm of the theophylline concentration in serum. A linear standard curve was constructed for the concentration range of theophylline from 2.5 µg/mL to 40 µg/mL, which includes the therapeutic range of 10-20 µg/mL. This range of concentration was that of the standards supplied in the theophylline kit.

The precisions of assay was estimated by measuring three serum samples with low (7.0 µg/mL), medium (16.1 µg/ML) and high (32.5 µg/mL) concentrations of theophylline determined by the Abbott FPIA method. Data are shown in Table 1. Each sample was analyzed 10 times for estimating intra-assay precisions. The inter-assay precisions were determined by analyzing theophylline at different concentrations on 10 different occasions (over 10 days).

TABLE 1

Intra- and Inter-Assay Imprecisions of Electrochemical EMIT Homogeneous EIA for Theophylline

| | Intra-assay | | Inter-assay | |
|---|---|---|---|---|
| Sample | Mean (SD), µg/mL | CV % | Mean (SD), µg/mL | CV % |
| 1 | 7.4 (0.7) | 9.1 | 6.3 (1.0) | 15 |
| 2 | 14.6 (1.3) | 8.8 | 16.0 (1.0) | 6.5 |
| 3 | 33.9 (2.8) | 8.2 | 31.7 (2.7) | 8.6 |

The analytical recovery for theophylline from normal serum was determined at concentrations of theophylline of 3.19, 6.38, 12.8, 25.5 µg/mL (Table 2), and at 7.50, 15.0, and 30.0 µg/mL from abnormal sera (Table 3). Percentage recovery was calculated as (measured therophylline/theophylline added)×100.

TABLE 2

Analytical Recovery of Theophylline Added to Normal Serum Pool

| Amount Added µg/mL | Amount Measured µg/mL | Recovery, % |
|---|---|---|
| 0 | detection limit | — |
| 3.19 | 2.89 | 90.6 |
| 6.38 | 6.17 | 96.7 |
| 12.8 | 12.4 | 96.9 |
| 25.5 | 23.4 | 91.8 |

Average analytical recovery = 94.0%

TABLE 3

Analytical Recovery of Added Theophylline from Abnormal Serum

| Mean Basal Concentration µg/mL | Theophylline Added µg/mL | Found (Basal + added) µg/mL | Recovery % |
|---|---|---|---|
| Hemolytic serum | | | |
| 8.5 | 7.50 | 16.3 | 105 |
| | 15.0 | 23.6 | 101 |
| | 30.0 | 39.3 | 103 |

TABLE 3-continued

Analytical Recovery of Added Theophylline from Abnormal Serum

| Mean Basal Concentration µg/mL | Theophylline Added µg/mL | Found (Basal + added) µg/mL | Recovery % |
|---|---|---|---|
| Icteric serum | 7.50 | 7.50 | 100 |
| 0 | 15.0 | 14.9 | 99.2 |
| | 30.0 | 29.8 | 99.3 |
| Lipemic serum | 7.50 | 8.01 | 107 |
| 0 | 14.3 | 15.8 | 111 |
| | 30.0 | 29.2 | 97.4 |

Average analytical recovery = 102.5%

This example teaches that the assay as described in the invention is precise and reproducible.

The data in Example 1 teach that the invention will give accurate data when spectophotometric interferences prevent obtaining accurate data in the FPIA method further substantiating the novelty of the invention.

EXAMPLE 2

Comparison of Methods

Figure 3:
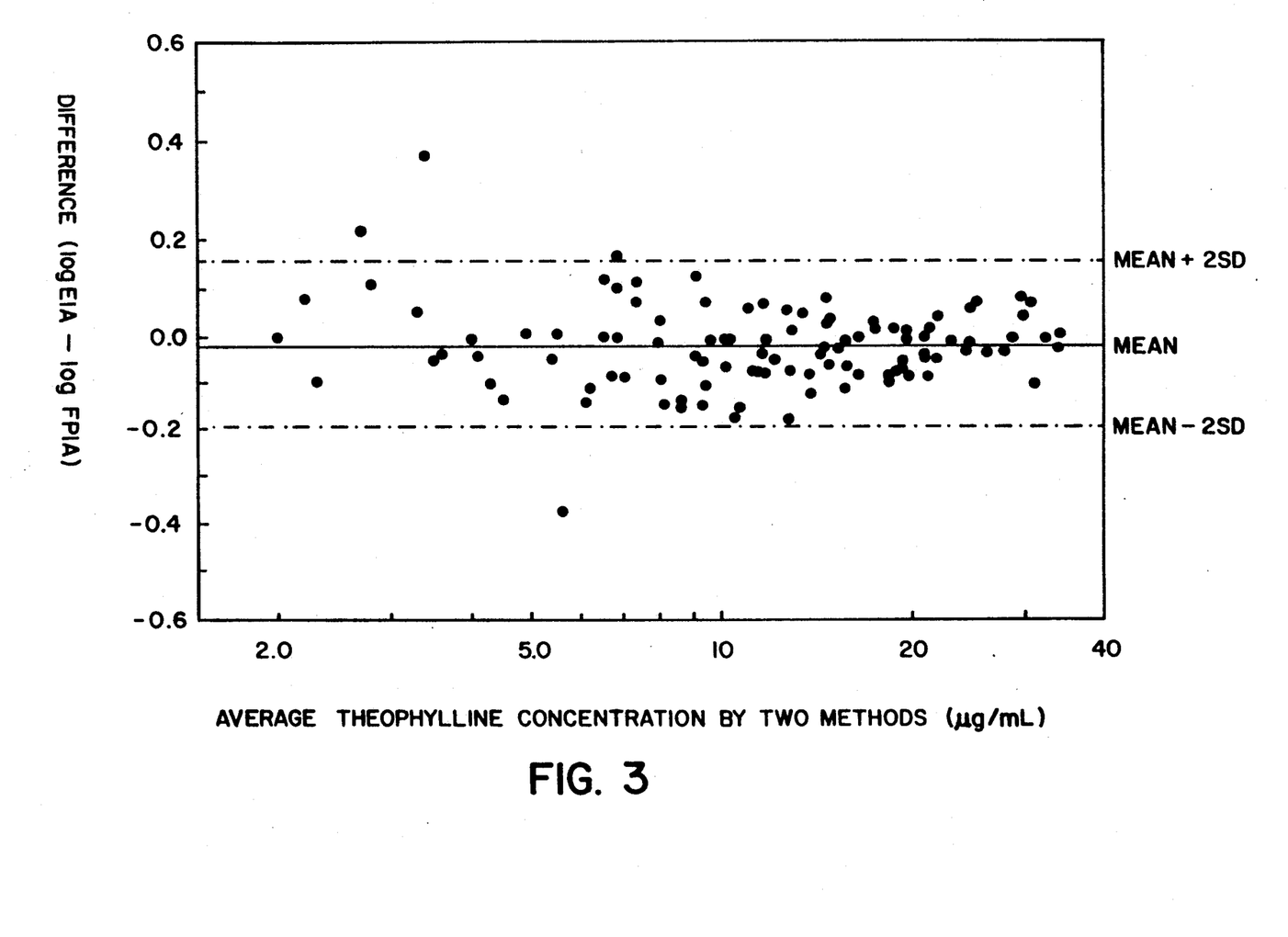
FIG. 3 is a graph showing the test results obtained from example 3.

Sera from 114 patients on theophylline therapy were collected and analyzed by the Abbott FPIA kit (Abbott Diagnostics, Abbott Park, Ill.) and the electrochemical method. Serum samples were analyzed by both procedures in the Toxicology Laboratory of University Hospital of Cincinnati (FIG. 3). Data were analyzed with Ligand Data Calculation (v 2.12e., David G. Rhoads Associates, Inc., Kennett Square, Pa.), which gave a linear regression equation of y=1.00×−0.57 (correclation coefficient r=0.966, mean values: 13.64 µg/mL for Abbott FPIA and 13.01 µg/mL for MIT EIA, t test: 3.14). For further evaluation of the method, the bias plot is presented in FIG. 3 to show the differences between corresponding measurements.

These data teach that the invention gives results comparable to other methods.

EXAMPLE 3

Whole blood samples were obtained by collecting in vacutainers containing EDTA. The procedures of assay were identical to those as described in Example 2 with the exception of the first dilution step, in which instead of diluting with tris buffer, 250 microliters of $H_2O$ were used to hydrolyze the red blood cells. All red blood cells were lysed, and the solution was homogeneous.

Figure 4:
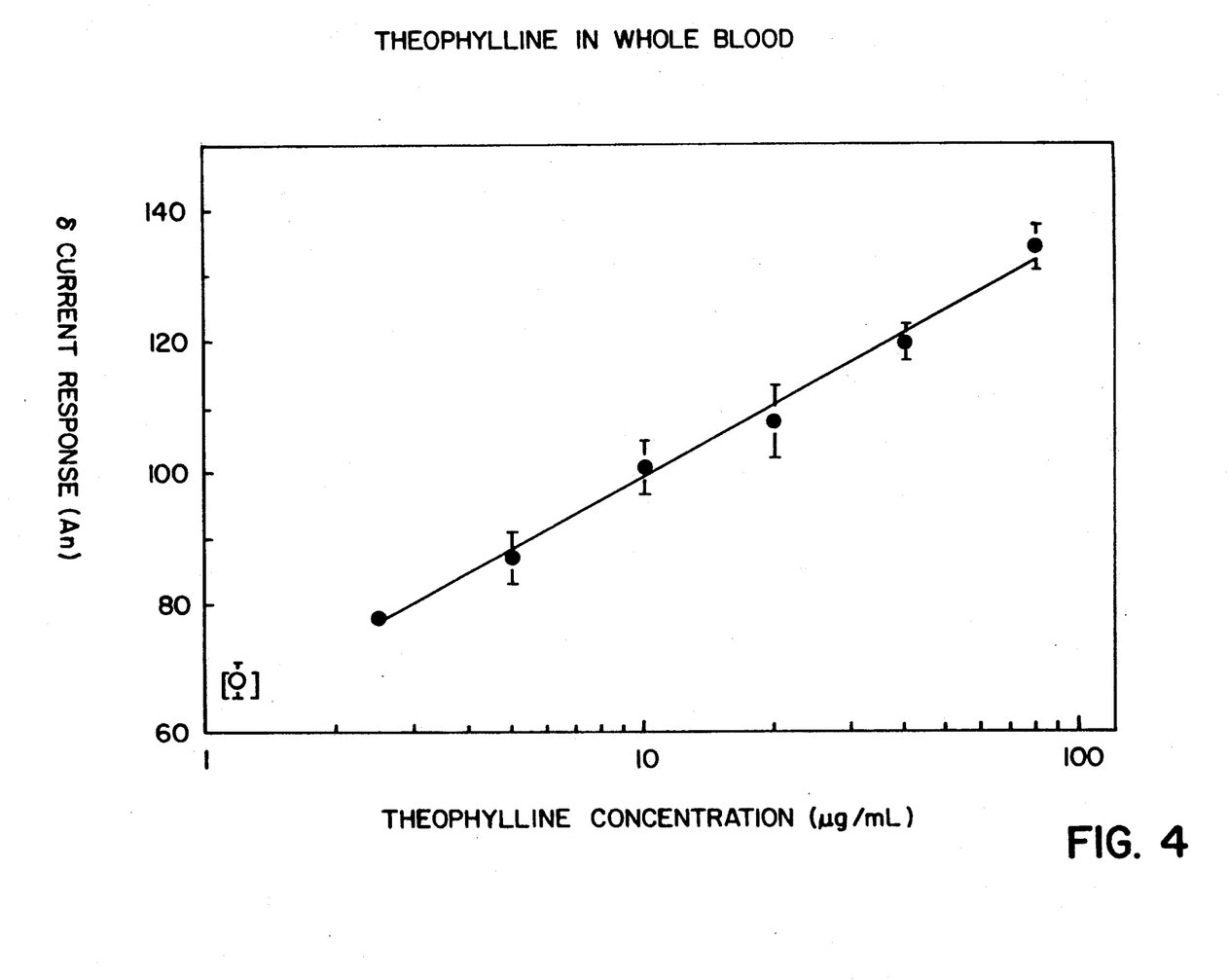
FIG. 4 is a graph showing the test results obtained in example 4.

Theophylline standards were made by adding stock theophylline aqueous solution to whole blood to obtain required concentration. FIG. 4 shows a typical standard curve with a linear range from 2.5 to 80 µg/mL of theophylline. This range of standard solutions encompasses the therapeutic range of theophylline in serum (10-20 µg/mL). The detection limit is about 2 µg/mL (blank+2SD), which is about the same as that of the electrochemical EMIT assay in serum.

This example teaches that the invention is applicable to whole blood analysis.

EXAMPLE 4

Ten consecutive duplicates of whole blood containing 80 µg/mL of theophylline were analyzed according to the embodiment of the invention as described in Example 3. The coefficient of variation for the current responses was 2.5%.

This example teaches that the invention yields reproducible analyses in the presence of whole blood.

EXAMPLE 5

Figure 5:
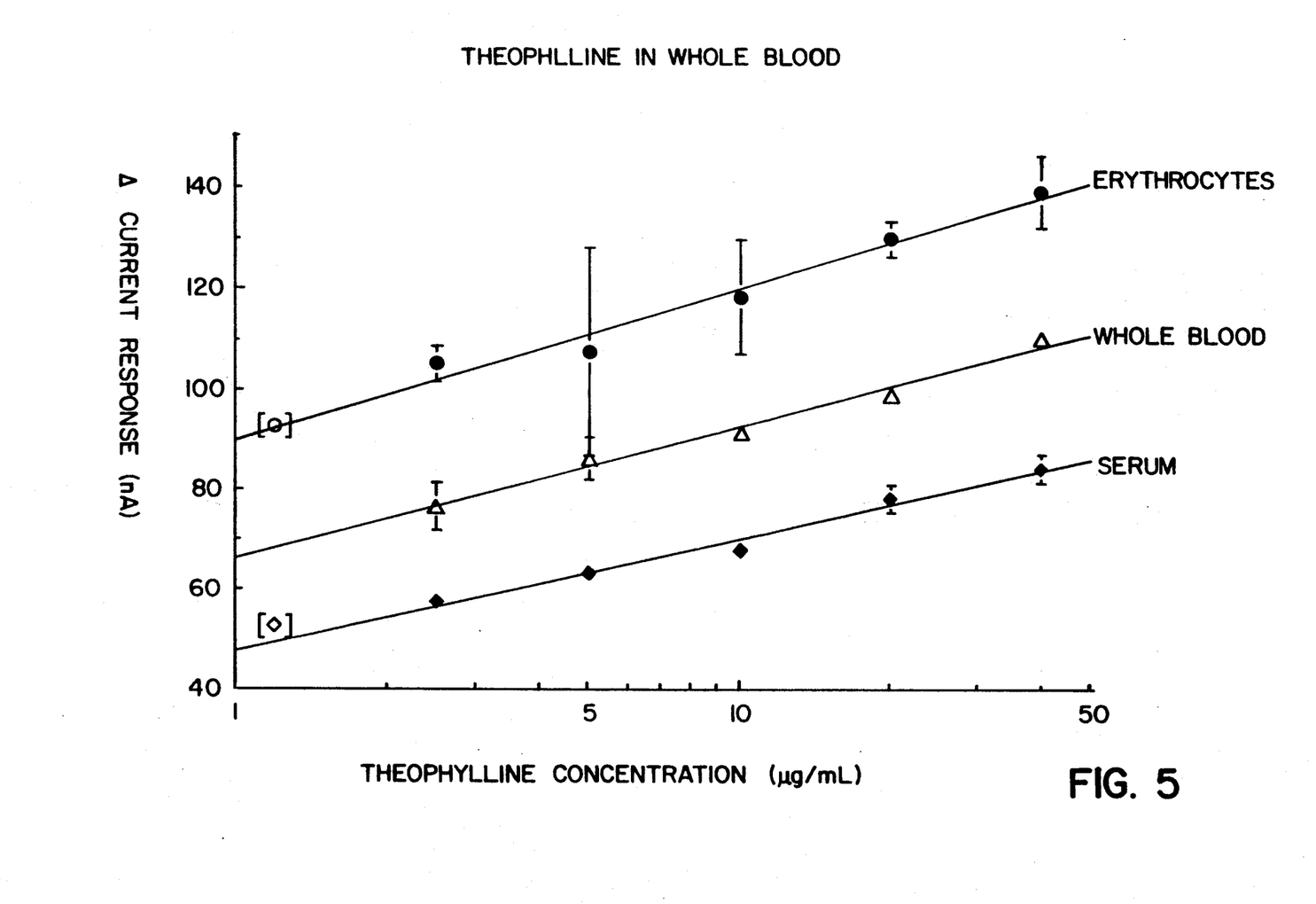
FIG. 5 is a graph showing the test results obtained in example 5.

FIG. 5 shows the electrochemical response versus theophylline doses in serum, whole blood and erythrocytes taken from the same person on the same day using the invention as described in Example 3. Although the intercept increases significantly in the order of serum, whole blood, and erythrocytes, the slope of the current response versus the theophylline doses is linear.

This example teaches that application of the invention yields a linear response that can be used to determine analytes in whole blood.

EXAMPLE 6

Comparison of 37 patients' samples measured by both the electrochemical method in whole blood and FPIA in serum yielded a regression equation of $C_{EIA}=0.95$ $C_{FPIA}-3.60$ (r=0.844). The good correlation coefficient shows the validity of the invention.

Examples 3-6 teach how application of the invention makes it possible to measure a drug in whole blood using a technique that was heretofore limited to serum.

EXAMPLE 7

EMIT phenytoin assay kits were purchased from Syva Co. Bovine serum albumin and NADH were from Sigma Chemical Co., St. Louis, Mo. 67138. EDTA was from Aldrich Chemical Co. Inc., Milwaukee, Wis. 53233. Phosphate buffer (0.1 mol/L, pH 7.0) was made from $K_2HPO_4$ and $KH_2PO_4$. Disposable 2.0-mL cups with a conical bottom (Fisher Scientific, Fair Lawn, N.J.; no. 02-544) were used to hold the enzyme reaction mixtures.

Phenytoin immunoassay. This homogeneous enzyme immunoassay for phenytoin is a sequential saturation method performed at room temperature. A two-point kinetic method was used sampling the enzyme reaction at 1 and 5 min; the difference in responses at the two times reflects the rate of NADH production for a given phenytoin concentration. For convenience, but not from necessity, each calibrator or unknown was processed in its entirety before assaying the next.

Assays were performed according to the manufacturer's instructions except that the reaction mixture was not aspirated into the spectrophotometer flow cell. Instead, two portions of the reaction mixture were added to separate aliquots of a DCIP solution at a timed interval and the redox reaction proceeded for a known time. Thus, at 1 and 5 min after the addition of Reagent B (enzyme-labeled phenytoin), 50 μL of the reaction mixture and 250 μL of pH 7.0 phosphate buffer were added to 300 uL of 0.42 mmol/L DCIP solution. The rate of NADH production was determined by injection of this reaction mixture, after 5 min, into the flow-injection analysis system for amperometric detection of $DCIPH_2$. Calibrators were assayed three times, unknowns once. Each assay took 11 min.

The NADH generated by glucose-6-phosphate dehydrogenase (G6PDH) was allowed to react with DCIP in a similar matrix. The kinetics of NADH production were then determined.

100 μL of substrate solution (glucose 6-phosphate and AND+) and 100 μL of "biological" matrix (per liter, 500 μmol of uric acid, 90 μmol of ascorbic acid, 200 mmol of acetaminophen, 1.0 mol of glutathione, 12 mg of cytochrome c, and 3.0 mmol of hemoglobin) was added to 1.5 mL of 2.5 mmol/L DCIP solution. Different amounts of the EMIT kit G6PDH-containing Reagent B (20, 50, and 100 μL) and phosphate buffer were then added to bring the final volume to 1.8 mL. 20 μL of the reaction mixture was injected at timed intervals and the production rates of NADH were thereby determined.

The production rate increases with increased G6PDH concentration. The plot of results for duplicate runs is linear (r=0.999). the results indicate that the detection of NADH produced from the enzyme is easily monitored by this method without any interference from the synthetic matrix.

The EMIT phenytoin assay depends on the competition of phenytoin and G6PDH-labeled phenytoin for a limited amount of specific antibody. The unbound enzyme-labeled phenytoin, in conjunction with G6P, converts NAD+ to NADH, while the bound enzyme is greatly inhibited.

The rate of $DCIPH_2$ production in the NADH-DCIP reaction can be used to evaluate the concentration of phenytoin by using a two-point method to determine the rate. The advantage of using the reaction rate of the response at a particular time is that it is not necessary to know when the enzymatic reaction starts. Thus, a change in current response over a particular time frame can be taken at any time after the addition of Reagent B. Also, if ascorbic acid and glutathione are present in the serum sample, their contribution to the overall current response is cancelled by using the rate method.

Serum samples from patients on maintenance phenytoin therapy were analyzed by the present invention and results (x) were compared with those of the FPIA (y) routinely used in the Toxicology Laboratory of University Hospital, Cincinnati. Analyses by the two methods were not performed on the same day. Analysis of the data by the Method Comparison Statistics Utility of Ligand Data Calc (v 2.12e; David G. Rhoads & Assoc., Kennett Square, Pa.) yielded a correlation coefficient of 0.95 (y=0.96×+1.44 mg/L, syx =0.07, n=23). Four low-concentration samples (2.5 mg/L) were also analyzed, and the results were in agreement with those of the FPIA. Thus, the method gives results that compare favorably with those of a currently used method for phenytoin in serum over a concentration range exceeding the therapeutic range, even in the presence of a wide variety of serum components.

This example demonstrates the electrochemical enzyme immunoassay of the model analyte phenytoin is feasible by flow-injection analysis incorporating DCIP as a redox coupling agent. It seems clear that the principle is applicable to any NADH-based analysis system. Good agreement with a routinely used FPIA procedure in the clinical laboratory was obtained for patients' serum samples. More importantly, electroactive species present in the serum samples do not pose any interference when the rate measurement is used.

It is a further advantage that the NADH product may be generated by a number of different coupled reactions and therefore may be used for a number of different analytes. This permits either the running of successive analyte assays on different analytes rapidly with a minimum adjustment of instrumentation from one assay to another, or the running of simultaneous assays with appropriate electrode configurations such as the interdigitated array.

Detection of the rate of production of appearance of the enzyme catalyzed reaction product is also advantageous because it minimizes interference effects from other substances present in the assay sample. Such interfering substances would have a constant effect on the current with time and thus do not affect the rate of current increase.

The sensitivity of the method of the invention is thus attributed to the combination of enzyme amplification and the minimization of interferences by performing the detection at a low potential, this latter being permitted by the use of the redox coupling agent.

Thus, the present invention is as versatile as photometric methods, yet requires no purification steps. This improves safety, reduces costs and should improve precision and accuracy. This has been a description of the present invention along with the preferred method of practicing this invention currently known. However, the invention should be defined by the appended claims wherein we claim:

We claim:

1. A method of detecting an analyte in a solution by reacting said analyte with an enzyme to form a concentration of a dinucleotide selected from the group consisting of NADPH and NADH quantitatively proportioned to the amount of said analyte in said solution;

wherein said analyte is selected from the group consistent of theophylline, phenytoin, lactic acid, carbamazepine, ethosuximide, phenobarbital, primidone, valoric acid, caffeine, digoxin, disopryram,iode, lidocaine, n-acetylprocainamide, procainamide, quinine, amikacin, chloramphenoicaol, gentamincin, netilmicin, vancomycin, amitriptyline, imipramine, desipramine, thyroxine, acetaminophen, amphetamine/methamphetamine, barbiturate, benzodiazepine, cannabinoid, cocaine, ethaqualine, emthadone, opiate, phencyclidine, and propoxyphene adding a concentration of a redox coupling agent selected from the group consisting of quinones, quinone amines, indophenols, phenazines, phenylene diimines and phenoxazines to said solution wherein said coupling agent has a redox potential of +400 to −200 millivolts versus a reference Ag/AgCl (3MKCl) electrode and wherein said concentration of said coupling agents is at least equal to the concentration of said dinucleotide whereby an electroactive coupling agent is formed in solution;

electrochemically detecting the concentration of said electroactive coupling agent thereby give an indication of the concentration of said analyte in said solution.

2. The method as claimed n claim 1 wherein said redox coupling agent has a redox potential of from about 0 to about 300 millivolts.

3. The method claimed in claim 1 wherein said coupling agent is a dichloroindophenol.

4. The method claimed in claim 1 wherein said redox coupling agent is 2,6 dichloroindophenol.

5. The method claimed in claim 4 wherein said test solution is a biological fluid.

6. The method claimed in claim 5 wherein said biological fluid is whole blood.

7. The method claimed in claim 1 wherein an amount of a surfactant effective to prevent protein present in said solution from coating an electrode is added to said test solution.

8. The method claimed in claim 7 wherein said test solution is diluted with an aqueous solution.

9. The method claimed in claim 8 wherein said solution has a pH of from about 2 to about 9.

10. The method claimed in claim 9 wherein said pH is about 7.

11. The method claimed in claim 10 wherein said redox coupling agent is permitted to react with said NADH for about 1 to about 10 minutes prior to detecting the electroactive coupling agent.

* * * * *

UNITED STATES PATENT AND TRADEMARK OFFICE
CERTIFICATE OF CORRECTION

PATENT NO. : 5,240,571
DATED : August 31, 1993
INVENTOR(S) : William R. HEINEMAN, Hua-Tang TANG, H. Brian HALSALL, Amadeo J. PESCE It is certified that error appears in the above-indentified patent and that said Letters Patent is hereby corrected as shown below:

In the drawings, Fig. 4, caption:

Delete "(An)" and insert in place there of --(nA)--.

In the specification:

Column 1, line 22, after "immunoassay" add --s--.

Colume 2, line 25, delete "where".

Column 3, line 30, delete dicucleotides" and insert in place thereof --dinucleotides--.

Column 3, line 39, delete "isocytric" and insert in place thereof --isocitrate --.

Column 3, line 40, after "AMP" insert --,--.

Column 3, line 40, delete "asparate" and insert in place thereof --aspartate--.

Column 3, line 42, delete "of".

Column 3, line 48, delete "Boerhinger" and insert in place thereof --Boehringer--.

Column 4, line 27, in the equation, delete "2AND" and insert in place thereof --2NAD--.

Column 4, line 33, delete "AND" and insert in place thereof --NAD--.

Column 5, line 9, delete "AND" and insert in place thereof --NAD--.

Column 5, line 19, after "microliter" add --s--.

Column 5, line 39, delete "AND" and insert in place thereof --NAD--.

Column 5, line 43, delete "AND" and insert in place thereof --NAD--.

UNITED STATES PATENT AND TRADEMARK OFFICE
CERTIFICATE OF CORRECTION

PATENT NO. : 5,240,571
DATED : August 31, 1993
INVENTOR(S) : William R. HEINEMAN, Hua-Tang TANG, H. Brian HALSALL, Amadeo J. PESCE It is certified that error appears in the above-indentified patent and that said Letters Patent is hereby corrected as shown below:

Column 7, line 23, delete "precisions" and insert in place thereof --precision--.

Column 7, line 48, delete "therophylline" and insert in place thereof --theophylline--.

Column 8, line 17, delete "spectophotometric" and insert in place thereof --spectrophotometric--.

Column 8, line 33-34, delete "correclation" and insert in place thereof --correlation--.

Column 9, line 54, delete "uL" and insert in place there of --µL--.

Column 9, line 65, delete "AND" and insert in place thereof --NAD--.

Column 9, last line, delete "was" and insert in place thereof --were--.

Column 10, line 10, delete the first "the" and insert in place thereof --The--.

UNITED STATES PATENT AND TRADEMARK OFFICE
CERTIFICATE OF CORRECTION

PATENT NO. : 5,240,571
DATED : August 31, 1993
INVENTOR(S) : William R. HEINEMAN, Hua-Tang TANG, H. Brian HALSALL, Amadeo J. PESCE It is certified that error appears in the above-indentified patent and that said Letters Patent is hereby corrected as shown below:

In the claims:

Column 11, lines 25-26, delete "consistent" and insert in place thereof --consisting--.

Column 11, line 28, delete "valoric" and insert in place thereof --valproic--.

Column 11, line 28-29, delete "disopryram,iode" and insert in place thereof --disopyram, iodide--.

Column 11, line 30, delete "chloramphenoicaol" and insert in place thereof --chloramphenicol--.

Column 11, lines 30-31, delete "gentamincin" and insert in place thereof --gentamicin--.

Column 11, line 35, delete "emthadone" and insert in place thereof --methadone--.

Column 12, line 13, delete "claimed n claim" and insert in place thereof --claimed in claim--.

Signed and Sealed this

Fifteenth Day of July, 1997

Attest:

BRUCE LEHMAN

*Attesting Officer*     *Commissioner of Patents and Trademarks*